United States Patent [19]

Bertelli

[11] Patent Number: 4,599,232

[45] Date of Patent: Jul. 8, 1986

[54] PHARMACEUTICAL COMPOSITION WITH METABOLIC AND ENERGETIC ACTIVITY FOR THE USE IN CARDIAC AND VASCULAR THERAPY

[75] Inventor: Alberto Bertelli, Milan, Italy

[73] Assignee: Sigma Tau Industrie Faramaceutiche Riunite S.p.A., Rome, Italy

[21] Appl. No.: 578,588

[22] Filed: Feb. 9, 1984

[30] Foreign Application Priority Data

Feb. 16, 1983 [CH] Switzerland ............................ 858/83

[51] Int. Cl.⁴ ..................... A61K 37/48; A61K 31/205
[52] U.S. Cl. ...................................... 424/94; 514/556; 514/690
[58] Field of Search ................. 424/329, 94; 514/556, 514/690

[56] References Cited

PUBLICATIONS

Fanelli—Chem. Abst., vol. 95 (1981), p. 12776g.
De Felice—Chem. Abst., vol. 88 (1978), p. 164,521p.
Abe et al—Chem. Abst., vol. 93 (1980), p. 197,847f.
Yamasawa et al—Chem. Abst., vol. 93 (1980), p. 197,857j.
Hakuta et al—Chem. Abst., vol. 93 (1980), p. 197,860e.

*Primary Examiner*—Sam Rosen
*Attorney, Agent, or Firm*—Walter H. Schneider

[57] ABSTRACT

The invention relates to a pharmaceutical composition containing carnitine or acetylcarnitine and Coenzyme $Q_{10}$ in ratios from 100:1 to 2:1, together with pharmaceutically acceptable eccipients.

The pharmaceutical composition described is suitable for the treatment of tissue energetic and metabolic disorders, and especially of heart and blood vessels, occurring in atherosclerosis, in myocardial or coronaric insufficiency, in hypertension, in cerebral ischaemia and, in general, tissue anoxia.

4 Claims, No Drawings

PHARMACEUTICAL COMPOSITION WITH METABOLIC AND ENERGETIC ACTIVITY FOR THE USE IN CARDIAC AND VASCULAR THERAPY

The present invention relates to a new pharmaceutical composition containing a combination of products used in tissue-metabolic and energetic biochemical process, such as Coenzyme $Q_{10}$ and carnitine or acetylcarnitine. Preferably, the composition according to the invention contains carnitine (or acetylcarnitine) in L form.

As it is well-known, carnitine is $\beta$-hydroxy-$\gamma$-trimethylamino butirric acid, whereas Coenzyme $Q_{10}$ stands for 2,3-dimethoxy-5-methyl-6-decaprenyl-benzoquinone.

The composition according to the invention is able to develop an effective therapeutic action in the prevention and treatment of atherosclerotic phenomena, in myocardial and coronary insufficiency, as well as in hypertension and in general in pathological conditions due to tissue anoxia.

L-carnitine is derived from lysine through steps including the transformation of $\epsilon$-N-trimethyl-lysine into $\gamma$-butyrrobetaine with the intervention of hydroxylase and proteino-methyl-transferase systems.

Already in 1952 it was observed (Carter et al.-Arch. Biochem. Biophys. 38-405-1952) that in the absence of carnitine Tenebrio moliter larvae died because of fat accumulation, and the explanation of this phenomenon can now be found through the biochemical observations concerning the carnitine function. Carnitine can be in fact acetylated at the expense of acetyl-CoA and it can stimulate the oxidation of fatty acids (Friedman S., Fraenkel G.-Arch. Biochem. Biophys., 59-491-1955).

Since carnitine is able to receive the acyl group of acyl-COA, is also able to provide this coenzyme for its catalytic functions and particularly for the Krebs cycle and thereby catalytically exerting an energetic function (Siliprandi N.-Biochem. J., 95-777-1965).

Coenzyme $Q_{10}$ also plays an important role in the cell energetic metabolism.

Coenzyme $Q_{10}$, in fact, serves as high mobility electrons carrier between the flavoproteins and the cytochromes of the respiratory system (Morton R. A., Nature 182-1764-1958; Gale P. et al., Arch. Biochem. Biophys., 93-211-1961).

The beta-oxidation processes of fatty acids take place in the mitochondrion and they need as enzymes FAD and NAD that are oxidized again by means of the respiratory system, where Coenzyme $Q_{10}$ acts as an essential element.

In turn fatty acids, in order to be able to cross the mitochondrial membrane, must be transformed into acyl-carnitine.

In short, therefore, carnitine lets the acyle groups cross the miochondrial membrane.

The carnitine system is therefore a shuttle system through which acyl-CoAs can go into and out of the mitochondrion without having to use energy. Once they are inside the mitochondrion, acyl-CoA are oxidized by means of $\beta$-oxidation process.

The biochemical processes binding at the different metabolic steps the action both of carnitine and of Coenzyme Q and that show the close interdependence of these two different systems for the cellular and tissutal and metabolic energetic function, also correlate with the biologic observation among the different activities that both carnitine and Coenzyme Q are able to carry out.

By means of the composition of the present invention it has been possible to notice the synergism that these two substances exert at the level of the myocardial functional capacity and coronaric circulation, and at the level of fat metabolism alterations and at vascular level.

The following pharmacological tests show the activity of the new pharmaceutical composition, and they point out the synergic effect obtained by the use of this composition.

Another aspect of the synergism resulting from the carnitine-Coenzyme Q association, is the one relating to the different activity of the two compounds in the prevention of many pathological conditions, such as, for example, tissue anoxia. On the one hand, in fact, carnitine, through the beta-oxidation of fatty acids, is able to restore the energy supplies necessary to cell-life, whereas Coenzyme Q is able to restore the ATP supplies necessary for the energetic metabolic processes of the cell.

The latter mechanism connected with Coenzyme Q action can be possibly attributed to its intervention at calcium ions level and to a block of their entry at mitochondrial level, which would imply a reduction of the ATP levels and also the activation of the proteinases subsequently leading to the destruction of cell-structures.

The effectiveness of the present invention is not, however, bound to the control of the biologic mechanisms so far exposed.

TOXICOLOGICAL TESTS

Both carnitine and Coenzyme Q do not possess a toxicity of their own if administered in association per os in the animal, as it had been possible to ascertain administering very high doses of Coenzyme and L-carnitine to Swiss mice and Wistar rats of both sexes. In fact, the administration per os of 1 g of Coenzyme Q associated to 1 g, 2 g, 5 g of carnitine did not cause any death in the animals thus treated.

Even the parenteral administration of high doses of associated carnitine and Coenzyme Q did not show any toxic effect or any kind of intolerance, and it was not possible in the same way, to ascertain a significant mortality in the animals with the injection of a composition containing mg 400 of Coenzyme Q and g 2 of carnitine.

Also the chronic toxicological tests (3 months) carried out both on Sprague-Dawley rats and in Beagle dogs (100 mg of Coenzyme Q and 500 mg of carnitine/day per os) confirmed the good tolerance and the lack of toxicity of the association Coenzyme Q-carnitine.

PHARMACOLOGICAL TEST

Tests on the Pitrexine-Induced Myocardial Anoxia

These tests showed how myocardial anoxia induced by the coronaric spasm caused by the venous administration of pitrexine in the rat could be inhibited by the administration of the Coenzyme Q-carnitine combination in comparison with the two individual components of the combination itself.

The venous injection of 1 unit/kg of pitrexine in the rat causes a coronaric spasm with subsequent decreased coronaric vascularization and myocardial oxygenization that can be electrocardiographically recorded through the characteristic T wave (Lindler's T wave).

From the tests that were carried out it was possible to ascertain that the administration of Coenzyme Q, contrary to the administration of carnitine only, decreases the amplitude of the T wave induced by the pitrexine injection, but that with the association of the two drugs (Coenzyme $Q_{10}$ mg 50+carnitine mg 250 i.p.) it is possible to obtain the virtual disappearance of this wave, that is the inhibition of the myocardial anoxic tissue processes.

It is therefore evident the synergism existing between the activity of carnitine and the activity of Coenzyme Q.

As a matter of fact, no rat treated with the Coenzyme Q-carnitine shows alterations against the T wave after administration of pitrexine, whereas more than 90% of the rats treated with carnitine only and more than 60% of the rats treated with Coenzyme Q only show this electrocardiographic sign due to the myocardial anoxia.

EVALUATION OF THE ANTIANOXIC CEREBRAL ACTIVITY

In order to evaluate the antianoxic activity also at a cerebral level, rabbits were used that were put into a close, airtight cage in which the air was subsequently substituted through nitrogen admission.

The re-admission of air in the cage can let the animal recover and keep it back to normality.

It is possible to evaluate the antianoxic activity of a substance by the comparison of the times necessary between control animals and treated animals for the anoxic electro-encepalographic signs to appear, as well as by the recovery-time necessary to achieve a normal electro-encephalogram after the air has been again re-admitted in the cage. The anoxia caused by the progressive substitution of the air with nitrogen produces electro-encephalographic alterations until electric silence is reached; these alterations are easily detectable by the electro-encephalogram.

In these tests we could ascertain that Coenzyme Q only (mg 50/kg i.p. or mg 200 per os) is able to induce a significant difference, between control groups and treated groups, of the time necessary for cerebral anoxia phenomena to appear, as well as for the recovery time necessary to go back to a normal electro-encephalogram: these times become thus much more significant, in case that carnitine is associated to Coenzyme Q (mg 250/kg i.p. or mg 500 per os), that by itself, in these tests, does not result to cause any significant shortening of the anoxia times.

From these tests the synergism between Coenzyme $Q_{10}$ and carnitine is therefore evident. Also the state of tissue anoxia caused by the serotonine injected at the root of the rat's tail, causing gangrene and necrosis of the tail itself, can be an effective test to measure the antianoxic capacity of different substances.

During these experiences, a group of Wistar rats were injected daily with 10 mg/kg of serotonine sulphate at the root of the tail. Whereas a group of animals was used as control-group, other groups of animals received simultaneously either Coenzyme Q (mg 100/kg) only per os by the parenteral route (mg 25/kg), or carnitine per os only (mg 100/kg) or by the parenteral route (mg 250/kg). Another group of animals received the two products associated both per os and by the parenteral route.

14 Days after the beginning of the treatment, both the time of appearance of cutaneous dyschromasia in the tail, and the appearance of gangrene and necrosis were calculated.

In none of the Coenzyme $Q_{10}$-carnitine combination treated animals, signs of gangrene or necrosis in the tail appeared, after fourteen days, whereas both in the Coenzyme $Q_{10}$ treated rats and in the rats treated with carnitine these signs were evident already seven days after the beginning of serotonine sulphate administration.

Also in this case, it is evident the synergism exerted by the two associated substances, Coenzyme Q and carnitine.

ANTIHYPERTENSIVE ACTIVITY

Rats which had been made experimentally hypertensive with the daily administration of mg 10 of DOCA (deoxycorticosterone acetate) five days a week for three consecutive weeks were used.

At the same time a 1% saline solution was administered to the animals.

A group of these animals, simultaneously to the DOCA solution, was treated with Coenzyme Q only, with carnitine only, and with the two products associated at the same doses as indicated in the previous tests.

After three weeks of treatment, the group of animals treated with DOCA showed arterial pressure values higher than 120 and the groups of animals treated with the two drugs, Coenzyme Q and carnitine associated did not show significant changes of the arterial pressure as compared with normal rats, whereas changes were evident both in the group of animals treated with Coenzyme Q and in the group of animals treated with carnitine; above all, no difference was detectable between the group treated with carnitine and the hypertensive rats control group.

TESTS ON THE INHIBITION OF THE EXPERIMENTAL ATHEROSCLEROTIC LESION

In these tests the capacity of the carnitine-Coenzyme Q combination was pointed out, in comparison with the two products administered individually, to prevent the incidence of tissue vasal lesions experimentally induced in the rat administering an atherogenic hypercholesteraemic diet having the following composition: casein 24%, cotton oil 10%, salt 5%, sugar 61%, cholesterol 0,5%, vitamin $D_2$ 200mUST/g diet).

After six weeks of this diet, all the animals were sacrificed, after dosing their plasma cholesterol, whereas aorta and heart were fixed and submitted to hystologic test.

Whereas the rats treated with the hypercholesteraemic and vitamina $D_2$ diet only, as well as the rats treated with this same diet and carnitine showed clear increases of hypercholesteraemia and serious lesions both at aortic and at myocardial level, the group of animals treated with the carnitine-Coenzyme Q combination (Coenzyme Q mg 50/kg per os, carnitine mg 500/kg per os) showed a definitely lower extent of such diet-induced atherosclerotic lesions.

The present invention also relates to all the aspects applicable in the industry connected with the use of the ubiquinon-carnitine combination in cardiovascular therapy.

A basic aspect of the present invention is therefore represented by pharmaceutical compositions containing an ubiquinoninc coenzyme, preferably Coenzyme $Q_{10}$, and carnitine or acetylcarnitine preferably in L forms, in ratios ranging from 1:100 to 1:2, in addition to other suitable eccipients in the form of, for example, capsules, tablets, pills, granulates, syrups, injectable solutions.

Some non-limitative examples of pharmaceutical compositions, that can be obtained with conventional methods of pharmaceutical procedure, are hereinafter reported.

Tablets containing 500 mg of acetyl L-carnitine and 10 mg of coenzyme $Q_{10}$.

Operculate capsules containing 500 mg of L-carnitine and 5 mg of Coenzyme $Q_{10}$.

Operculate capsules containing 250 mg of L-carnitine and 50 mg of Coenzyme $Q_{10}$.

Pills containing 50 mg of L-carnitine and 25 mg of Coenzyme $Q_{10}$.

I claim:

1. A pharmaceutical composition having metabolic antianoxic activity containing as the principal active ingredient an antianoxic effective amount of a combination comprising the components Coenzyme $Q_{10}$ and a quaternary ammonium compound selected from carnitine and acetylcarnitine in admixture with a pharmaceutically acceptable carrier, said components being in a synergistic antianoxic active ratio.

2. A pharmaceutical composition according to claim 1 in which the Coenzyme $Q_{10}$ and the quaternary ammonium compound are in a ratio of from 1:100 to 1:2 parts by weight.

3. A pharmaceutical composition according to claim 2 in which the quaternary ammonium compound is carnitine in L-form.

4. A pharmaceutical composition according to claim 2 in which the quaternary ammonium compound is acetyl-L-carnitine.

* * * * *